United States Patent [19]

Bradley

[11] Patent Number: 4,561,830
[45] Date of Patent: Dec. 31, 1985

[54] LINEAR PERISTALTIC PUMP

[75] Inventor: John Bradley, Encinitas, Calif.

[73] Assignee: IVAC Corporation, San Diego, Calif.

[21] Appl. No.: 655,758

[22] Filed: Oct. 1, 1984

[51] Int. Cl.[4] .................... F04B 43/12; F04B 45/08
[52] U.S. Cl. ................................................ 417/474
[58] Field of Search ............... 417/474, 475, 478, 479, 417/480, 510

[56] References Cited

U.S. PATENT DOCUMENTS

| | | | |
|---|---|---|---|
| 2,546,852 | 3/1951 | Corneil | 417/474 X |
| 2,877,714 | 3/1959 | Sorg et al. | 417/474 |
| 3,427,986 | 2/1969 | Corneil | 417/474 |
| 3,658,445 | 4/1972 | Pulman et al. | 417/474 |
| 3,778,195 | 12/1973 | Bamberg | 417/474 |
| 3,798,982 | 3/1974 | Lundquist | 74/53 |
| 4,191,184 | 3/1980 | Carlisle | 128/214 |
| 4,236,880 | 12/1980 | Archibald | 417/478 |
| 4,277,226 | 7/1981 | Archibald | 417/38 |
| 4,373,525 | 2/1983 | Kobayashi | 128/214 |
| 4,410,322 | 10/1983 | Archibald | 604/153 |
| 4,472,117 | 9/1984 | Wenstrup | 417/477 |

Primary Examiner—Richard E. Gluck
Attorney, Agent, or Firm—Fulwider, Patton, Rieber, Lee & Utecht

[57] ABSTRACT

The invention relates to a peristaltic pump wherein a plurality of cam actuated fingers are adapted to pump fluid through a flexible tube by sequentially closing off the fluid filled tube along a length thereof. The fingers are mounted to rotate on a common axis and are spaced from one another in order to reduce the power requirement for operating the pump. A rigid, spring loaded pressure pad, preferably mounted on the same axis as the cam actuated fingers, maintains essentially the same pressure on each of the fingers as they close off the adjacent portion of the tube.

11 Claims, 10 Drawing Figures

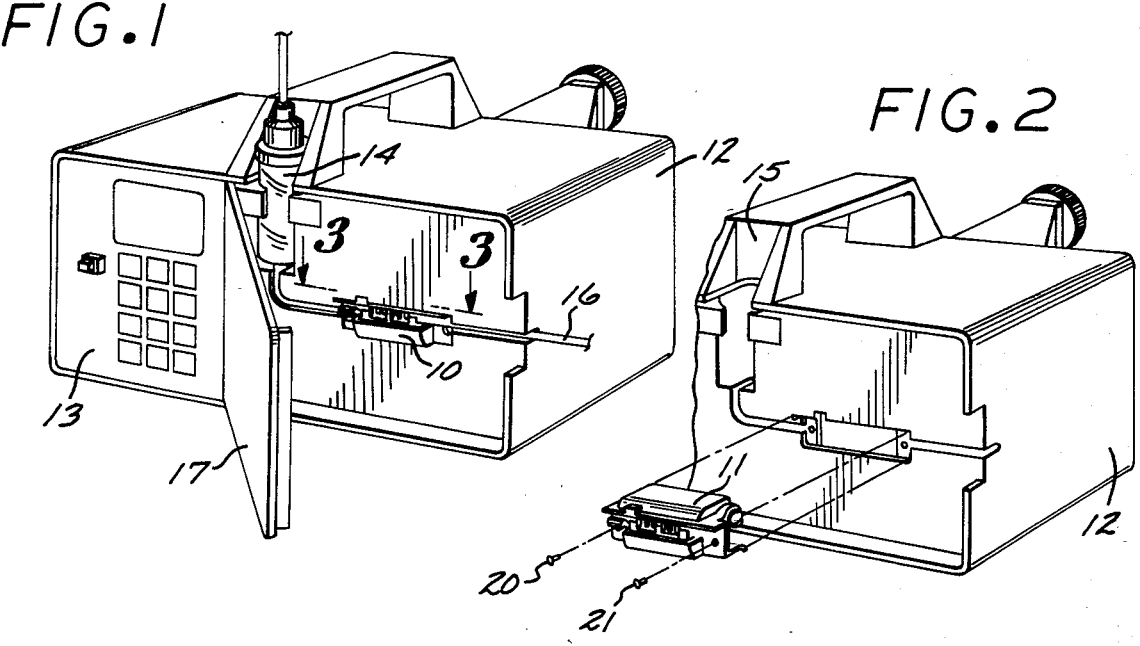
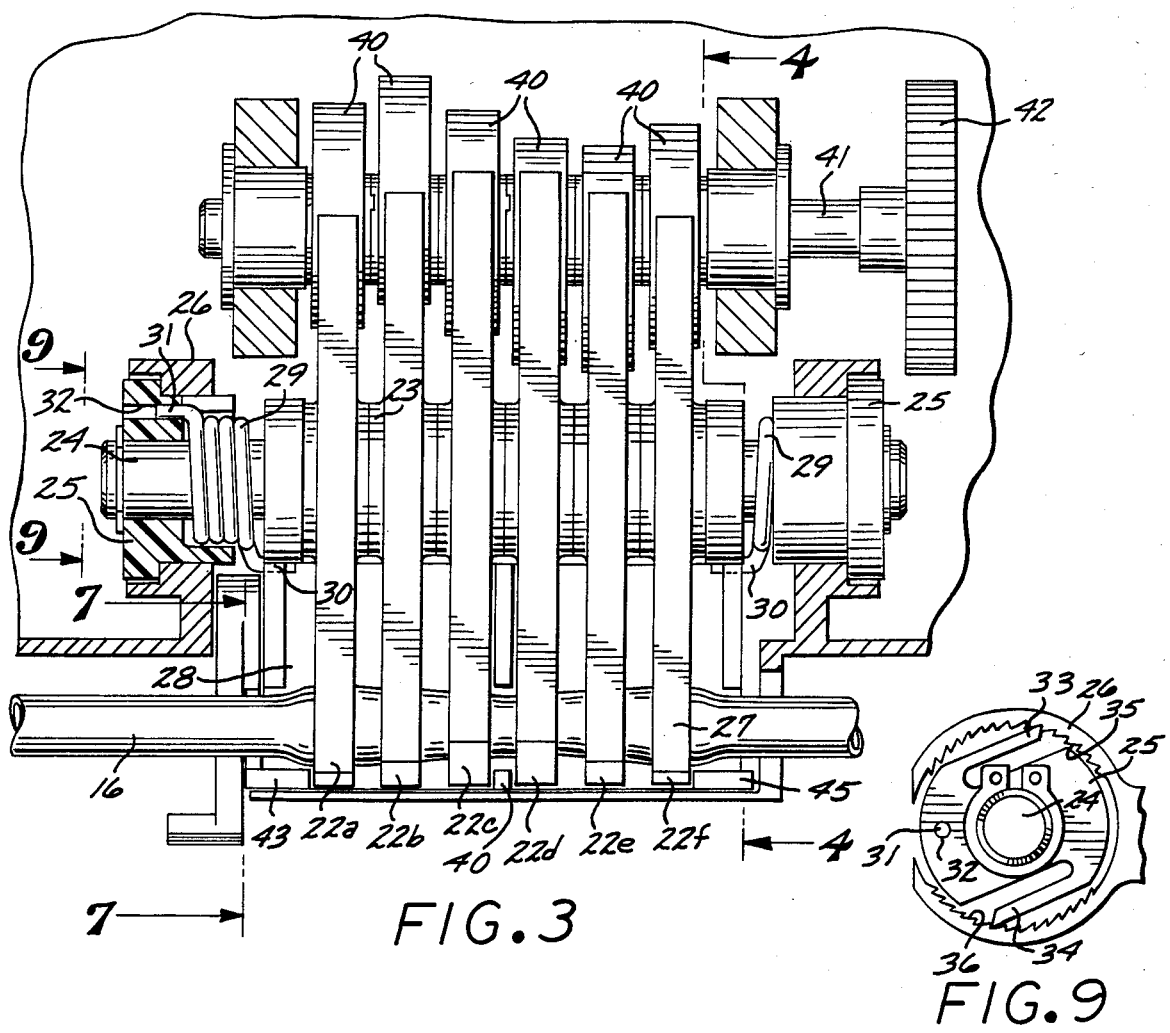

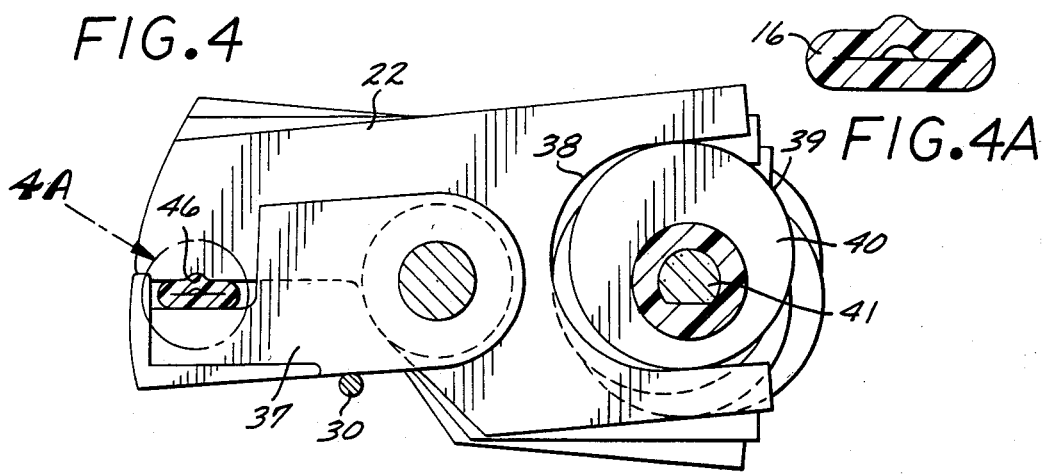
FIG. 4
FIG. 4A
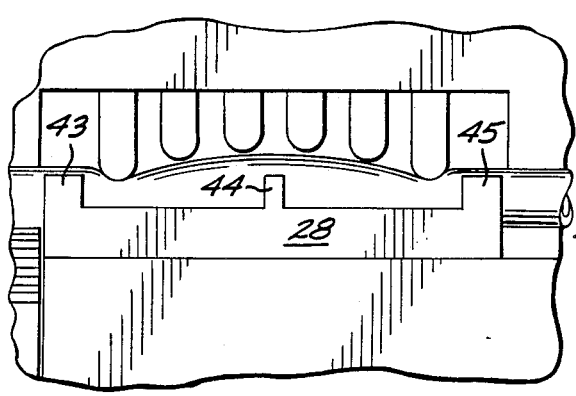
FIG. 5
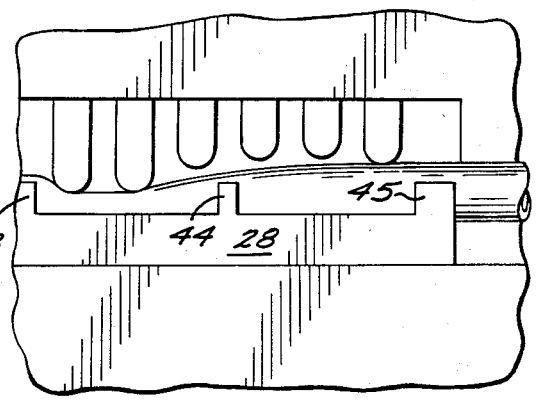
FIG. 6
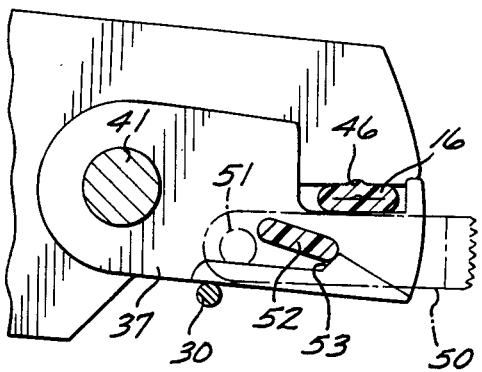
FIG. 7
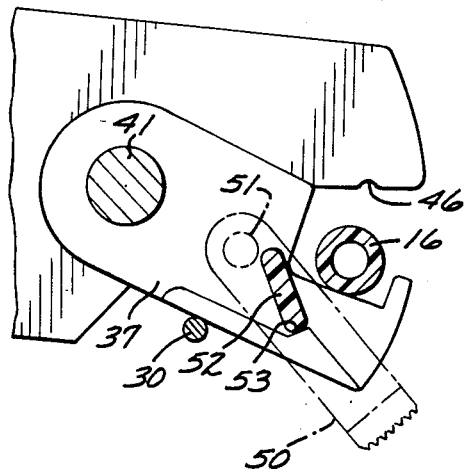
FIG. 8

LINEAR PERISTALTIC PUMP

BACKGROUND OF THE INVENTION

This invention generally relates to a linear peristaltic pump for the IV administration of parenteral fluids such as saline and drug solutions, and for enteric administration of fluids such as liquid nutrients.

One of the most important aspects of the administration of parenteral fluids is controlling the fluid flow rate to the patient. In prior practices where the fluid was drained from an inverted bottle and fed by gravity through a clear plastic IV tube to the patient, fluid flow was usually controlled by adjusting the position of a roll clamp on the IV tube. The fluid flow rate was determined by counting the fluid drops in a drip chamber over a period of time and then, if needed, the position of the roll clamp was adjusted to obtain the desired flow rate. However, this gravity fed administration system was subject to large flow rate variations due to changes to the liquid level in the bottle, changes in the temperature of the fluid, changes in the venous or arterial pressure in the patient, patient movement and drift in the effective setting of the roll clamp. As a result, frequent monitoring by medical personnel was required and variations were still encountered.

Electronic pump systems and drop flow controllers for gravity systems helped in maintaining a desired flow rate of parenteral fluids to the patient and such systems are now in widespread use. As the mechanical arts were developed, new applications have evolved which have placed more difficult demands on the delivery systems. As a consequence, the need for improvement continues to exist.

Prior pumping systems, particularly linear peristaltic pumping systems, provided a much more consistent fluid flow, particularly with viscous fluids which were not readily controllable in a gravity administration system. Typical pumping systems now in use have a plurality of cams, an equal number of cam actuated fingers or cam followers and a pressure pad adapted to receive a flexible tube and urge the tube against the fingers or cam followers. When the fingers or cam followers were sequentially actuated by the cams, the individual fingers would deform and close off the tube at a plurality of sequential points along the length of the tube to thereby force fluid in the tube along the length thereof.

While the prior linear peristaltic pumping system described provided a more consistent fluid flow than with the roll clamp approach, the energy requirements for pumping were relatively high because of the friction between the fingers themselves and between the fingers and the cams which activate the fingers. Additionally, the prior systems characteristically had a relatively low pump efficiency because of leakage or backflow of fluids.

Moreover, it is required that the fingers exert sufficient force to achieve delivery under a number of variable conditions. These conditions relate to entering stiffness, the viscosity of the fluid being delivered and the resistance of the patient's system. In addition, it is desirable to limit the pressure developed in the delivery system should an occulsion occur in that system, such as from a kinked tube.

It is evident that there is a recognized need for a relatively simple peristaltic pump which has high mechancial and pumping efficiencies which will deliver fluids accurately within desired operating limits. The present invention satisfies these needs.

SUMMARY OF THE INVENTION

The present invention is directed to a linear peristaltic pump for the administration of parenteral fluids which has improved pumping efficiency, requires less energy to operate and prevents discharge pressures from exceeding predetermined limits should the discharge line become blocked.

The peristaltic pump in accordance with the present invention is provided with a plurality of cams, an equivalent number of cam actuated fingers or followers and a pressure pad to urge a flexible tube against the individual fingers to effect fluid flow in much the same manner as the prior devices. However, the improvement of the invention involves rotatably mounting the fingers on a common axis or shaft so that the fingers or cam followers are rotated through a small arc when actuated by the movement of the cam surface to thereby urge the fingers against the tube to close off the tube in a sequential manner so as to force liquid through the tube.

The pressure pad is preferably rotatably mounted on the same common axis or shaft as the fingers and is spring loaded toward the fingers so the pad is urged against the tube to close off the tube when the individual cam operated fingers are at their maximum point of travel. The pressure pad is rigidly constructed and firmly mounted so that little or no rocking thereof occurs during the sinusoidal movement of the fingers as they sequentially close off the tube along the length thereof. In this manner, essentially the same pressure is urged against each of the fingers as they close off the tube. As each finger reaches the apex, its maximum position and then begins to recede, the spring loaded pressure pad maintains sufficient pressure to pinch off the tube until the next finger in sequence pinches off the tube and pushes the pressure pad back to the original position as the next cam follower reaches its maximum position. In this manner the fluid leakage, which was characteristic of most prior linear peristaltic pumps, is eliminated. The number of fingers or cam followers required for effective pumping is also reduced.

In a preferred embodiment of the invention, the surfaces of each of the fingers which comes in contact with and closes off the IV tube is provided with a groove in line with tube, in order to prevent pressure buildup beyond predetermined limits. When the fluid pressure within the tube exceeds a predetermined limit, it forces the wall of the IV tube into the groove, thereby relieving some of the pressure by allowing backflow in the tube toward the inlet side of the pump. When the pressure in the tube is reduced to a level below the maximum desired, the tube wall pulls away from the groove and assumes its normal cross section.

To reduce the energy required to operate the pump, the fingers are spaced from one another to minimize sliding friction therebetween. The desired spacing is best obtained by making the hubs of the fingers thicker than the body of the finger. Preferably, the fingers are made of materials having low coefficient of friction such a polytetrafluoroethylene sold under the trademark Teflon ®.

These and other advantages of the present invention will become more apparent in the following detailed description of the invention taken in conjunction with the exemplary drawings.

BRIEF DESCRIPTION OF THE DRAWINGS

FIG. 1 is a perspective view of a pumping system which embodies features of the invention.

FIG. 2 is a partial perspective view as shown in FIG. 1, illustrating the method for mounting the pumping element.

FIG. 3 is a plan view taken partially in section illustrating the pumping mechanism.

FIG. 4 is an elevational view showing the mounting and movement of the cam actuated fingers of the pumping element.

FIG. 4A is a cross-sectional view of the flexible tube when compressed under internal pressure.

FIGS. 5 and 6 illustrate the peristaltic action of the fingers on a flexible tube disposed within the pumping IN device.

FIGS. 7 and 8 illustrate the action of the rigid pressure pad to facilitate insertion of the tube within the pumping element.

FIG. 9, taken along the view 9—9 shown in FIG. 3, which illustrates the ratchet and pawl mechanism on the shaft about which the cam actuated fingers pivot.

DETAILED DESCRIPTION OF THE INVENTION

In the accompanying illustrative drawings, a linear peristaltic pump is shown which embodies features of the present invention.

As shown in FIG. 1, a linear peristaltic pump 10 contained in a housing 11 is installed in a cabinet 12 which also contains the controls for the pump 10. The control panel generally shown at 13 allows for the selection of flow rates and other fluid administration parameters. A drip chamber 14 is seated in the recess 15 provided in the cabinet 12 and flexible IV tube 16 leads from the drip chamber 14 through the peristaltic pump 10 and out of the cabinet 12 to a patient (not shown). A cabinet door 17 is provided to protect the pump 10 after the drip chamber 14 and IV tube 16 have been installed and while the pump 10 is being operated.

FIG. 2 illustrates the ease and simplicity of the installation and removal of the pump housing 11 for cleaning and maintenance. Screws 20 and 21 are removed and then pump housing 11 may be pulled out of the cabinet 12.

The components of the pump 10 and the operation thereof are best shown in FIG. 3. The individual fingers 22a-f are rotatably mounted through the hubs 23 thereof on a common shaft 24. T-shaped collars 25 are fixed at both ends of shaft 24 and adapted to be fixed in and supported by brackets 26 which are preferably formed integral with the pump housing 11. The hubs 23 of fingers 22 are thicker than the body 27 thereof in order to space the fingers 22 from one another and thereby minimize sliding friction between the fingers. Pressure pad 28 is also mounted on shaft 24 and is urged to pivot in the direction of the fingers by means of the helical springs 29 on both ends of the shaft 24. One end 30 of each of the springs 29 fit under the arms 37 of the pressure pad 28 to push the pad 28 in the desired direction. The other end 31 of each of the springs 29 fit into the aperture 32 in collars 25. As shown in FIG. 9, collars 25 are provided with pawls 33 and 34 which interfit with the racheted surfaces 35 and 36 provided in the bracket 26 to thereby lock the collar 25 and the end 31 of the springs 29.

Each of the fingers 22 are provided with semi-circular shoulders 38 at the ends thereof which ride on the operative surfaces 39 of a plurality of circular cams 40. The cams 40 are mounted on shaft 41 offset from their centers and are rotated from one another on the shaft 41 by an angle equal to 360°/n, where n is the number of cams 40. Cam shaft 41 is driven by gear 42 which is driven by means not shown.

When the cam shaft 41 is rotated, the individual cams 40 which interfit into the semicircular shoulders 38 of the fingers 22 causes the ends of the fingers 22 in contact therewith to oscillate or rotate back and forth through a small arc about the axis of shaft 24 sequentially. As a result, the fingers 22 sequentially constrict the IV tube 16 to thereby move a discrete quantity of fluid therethrough.

The pressure pad 28 is formed with relatively thick sections so that it will remain rigid and will not bend significantly during the operation of the pump. The arms 37 thereof are firmly but rotatably or pivotally mounted on shaft 24 so the pad 28 is constrained to only rotate or pivot axially about the shaft so that each of the fingers pinches or closes off the tube 16 as it comes into contact therewith with essentially the same pressure. The pressure pad 28 has little tendency to rock as the fingers 22 sequentially move along the length of the tube 16. Tube guides 43, 44 and 45 are provided to ensure proper positioning of the tube 16 on the pressure pad 28.

The peristaltic activity of the pump 10 is shown in FIGS. 5 and 6. The tube 16 closed off by at least one finger 22 at all times. When one of the fingers, for example 22f, has reached its maximum movement and begins to recede as shown in FIG. 5, the following finger 22a will close off the tube 16 before the first finger 22f has moved sufficiently to open the passageway of the tube 16. The following finger continues to its maximum movement with the pressure on the tube 16 by the pressure pad 28 being sufficient to keep the tube 16 closed. As the fingers 22 close the tube 16 at sequential points along a length thereof, a discrete body of fluid is driven through the tube 16. In this manner, there is essentially no leakage or backflow of fluid toward the inlet side of the pump 10 which was characteristic of prior pumps. Moreover, although the pumping acton is peristaltic in nature, the output pressure of the pump is relatively constant. The output pressure must be sufficient to overcome resistance to flow in the tube and the discharge elements and the back pressure from teh patient's vascular system.

During the operation of the pump, should the discharge side of tube 16 be partially or completely blocked, the pressure in the tube can build up to undesirable levels. To minimize such pressures outside of a desired operating range, pressure relieving grooves 46 are provided on the working surfaces of each of the fingers 22 and, as shown in FIG. 4, the grooves straddle the center of the tube 16. When the pressure exceeds the predetermined maximum desired levels, the flexible tube expands into the groove as shown in FIG. 4A thereby allowing backflow of fluid toward the inlet side of the pump 10 and thereby lowering the pressure to more desirable levels. The size and shape of the groove is predetermined so that the maximum pressure within the tube will not exceed some desirable limit. The width and depth of the groove is dependent upon the material characteristics and the wall thickness of the pump tube segment and the pressure limit required for the pump.

The shape of the groove is preferably a smooth arc because sharp corners tend to prevent the complete closure of the tube when the pressure is ultimately reduced.

As shown in FIGS. 7 and 8, the pressure pad 28 is raised and lowered by means of a lever 50 which is supported on shaft 51 fixed to the pump housing 11, thereby allowing the insertion and removal of tube 16 into pump 10. A projecting element 52 on the lever 50 rides on the shoulder 53 on the side of the pressure pad 28 so that the lever 50 is pushed downwardly the pressure pad is moved away from the fingers 22. When the end of the projecting element 52 rides over the edge of shoulder 53 pressure pad 28 is locked in the open position as shown in FIG. 8. Because of the spring loading of the pressure pad 28, it will move into position urging the tube 16 into contact with the fingers 22 as shown in FIG. 7 when the lever 50 is pushed far enough so that the projecting element slides over the shoulder 53. In this manner, so the tube 16 is inserted in the pump and the pressure pad 28 is released to urge the tube against the fingers 22, at least one of the fingers 22 closes off the tube 16 so that there is no leakage of fluid through the tube 16 when the pump 10 is not operating.

The fingers 22 are spaced from one another on shaft 24 by the thick hubs 23 thereof. As a result, there is little sliding contact between the individual fingers 22 and thus there is a considerable reduction in the power required to drive the pump. By making the fingers of materials having low frictional properties, even more significant reductions in power requirements can be made.

The pumping device of the invention is very simply designed for low cost production and for easy cleaning and maintenance. The device will reliably and accurately pump the desired amount of fluid with very little variation. Pump efficiency is high desired operating limits are maintained.

Other modifications and improvements can be made to the invention without departing from the inventive concepts thereof.

I claim:

1. In a linear peristaltic pump having a plurality of cams, a plurality of cam actuated fingers adapted to be moved back and forth by said cams a pressure pad adapted to receive a flexible tube and to urge the flexible tube toward the individual fingers so that when the fingers are sequentially actuated by the cams to contact and close off the flexible tube at a plurality of sequential locations on the tube, fluid is forced along the length of the tube, the improvement comprising:

the plurality of cam actuated fingers pivotally mounted on a common axis so that when actuated by the cams each of said fingers are pivoted about the common axis to sequentially contact and close off the tube, and the pressure pad being of rigid construction and being firmly mounted to pivot about an axis having the same orientation as the axis on which the fingers are mounted so that essentially no rocking of the pressure pad occurs along the longitudinal axis of the tube when the fingers contact and close off the tube.

2. The linear peristaltic pump of claim 1 wherein the pressure pad is pivotally mounted on the same axis as the fingers.

3. The linear peristaltic pump of claim 2 wherein the pressure pad and the fingers are mounted on a common shaft.

4. The linear peristaltic pump of claim 3 wherein the pressure pad is spring loaded on the shaft to close in the direction of the fingers.

5. The linear peristaltic pump of claim 1 wherein the fingers have pressure relieving grooves in the surfaces thereof which contact the flexible tube.

6. The linear peristaltic pump of claim 1 wherein the cams are circular and the fingers are provided with semi-circular shoulders which are adapted to ride on the operative surface of the circular cams adjacent thereto.

7. The linear peristaltic pump of claim 1 wherein the fingers are mounted on a shaft and are spaced from one another along the length of the mounting shaft by means of integral hubs which are thicker than the body of the fingers.

8. The linear peristaltic pump of claim 6 wherein the fingers are made of materials having low frictional properties.

9. The linear peristaltic pump of claim 1 in which the pressure pad urges the flexible tube toward the cam actuated fingers so that at least one finger closes off the tube along the length thereof in the pump.

10. In a linear peristaltic pump having a plurality of cams, a plurality of cam actuated fingers adapted to be moved back and forth by said cams and a pressure pad adapted to receive a flexible tube and to urge the flexible tube toward the individual fingers so that when the fingers are sequentially actuated by the cams to contact and close off the flexible tube at a plurality of sequential locations on the tube, fluid is forced along the length of the tube, the improvement comprising:

the pressure pad being of rigid construction, being firmly mounted to pivot about an axis parallel to the tube on the pressure pad so that essentially no rocking of the pressure pad occurs along the longitudinal axis of the tube while the fingers seqentially contact and close off the tube and being spring loaded to close so that the pressure pad can be pivoted away from the cam actuated fingers to facilitate inserting the flexible tube therebetween and so that upon the release of the pressure pad, the pressure pad urges the tube toward the cam actuated fingers.

11. The linear peristaltic pump of claim 10 wherein after the flexible tube is inserted and the pressure pad is released, at least one of the fingers closes off the tube in order to prevent leakage of fluid through the tube when the pump is not operating.

* * * * *